US007925511B2

(12) United States Patent
Li et al.

(10) Patent No.: US 7,925,511 B2
(45) Date of Patent: Apr. 12, 2011

(54) SYSTEM AND METHOD FOR SECURE VOICE IDENTIFICATION IN A MEDICAL DEVICE

(75) Inventors: Li Li, Milpitas, CA (US); Clark R. Baker, Jr., Newman, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 979 days.

(21) Appl. No.: 11/540,242

(22) Filed: Sep. 29, 2006

(65) Prior Publication Data
US 2008/0082339 A1 Apr. 3, 2008

(51) Int. Cl.
*G10L 15/00* (2006.01)

(52) U.S. Cl. ............... 704/271; 704/275; 607/2; 607/46

(58) Field of Classification Search ............... 704/271, 704/275; 607/2, 46
See application file for complete search history.

(56) References Cited

U.S. PATENT DOCUMENTS

| | | |
|---|---|---|
| 3,638,640 A | 2/1972 | Shaw |
| 4,621,643 A | 11/1986 | New, Jr. et al. |
| 4,653,498 A | 3/1987 | New, Jr. et al. |
| 4,700,708 A | 10/1987 | New, Jr. et al. |
| 4,714,341 A | 12/1987 | Hamaguri et al. |
| 4,770,179 A | 9/1988 | New, Jr. et al. |
| 4,805,623 A | 2/1989 | Jöbsis |
| 4,869,254 A | 9/1989 | Stone et al. |
| 4,911,167 A | 3/1990 | Corenman et al. |
| 4,936,679 A | 6/1990 | Mersch |
| 4,972,331 A | 11/1990 | Chance |
| 5,078,136 A | 1/1992 | Stone et al. |
| 5,119,815 A | 6/1992 | Chance |
| 5,122,974 A | 6/1992 | Chance |
| 5,167,230 A | 12/1992 | Chance |
| 5,297,548 A | 3/1994 | Pologe |
| 5,351,685 A | 10/1994 | Potratz |
| 5,355,880 A | 10/1994 | Thomas et al. |
| 5,368,026 A | 11/1994 | Swedlow et al. |
| 5,372,136 A | 12/1994 | Steuer et al. |
| 5,385,143 A | 1/1995 | Aoyagi |
| 5,482,036 A | 1/1996 | Diab et al. |

(Continued)

FOREIGN PATENT DOCUMENTS
DE 19932147 A1 1/2001
(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10$^{th}$ Annual International Conference*, CH2566-88, vol. 88, pp. 1781-1782 (1988).

(Continued)

*Primary Examiner* — Daniel D Abebe (57) ABSTRACT

There is provided a system and method for secure voice identification in a medical device. More specifically, in one embodiment, there is provided a method comprising receiving an audio signal, identifying one or more frequency components of the received audio signal, determining a permission level associated with the one or more frequency components, determining a medical device command associated with the one or more frequency components, wherein the medical device command has a permission level, and executing the medical device command if the permission level of the medical device command is at or below the permission level associated with the one or more frequency components.

24 Claims, 6 Drawing Sheets

U.S. PATENT DOCUMENTS

| | | | |
|---|---|---|---|
| 5,533,507 A | 7/1996 | Potratz | |
| 5,553,614 A | 9/1996 | Chance | |
| 5,564,417 A | 10/1996 | Chance | |
| 5,575,285 A | 11/1996 | Takanashi et al. | |
| 5,630,413 A | 5/1997 | Thomas et al. | |
| 5,645,059 A | 7/1997 | Fein et al. | |
| 5,645,060 A | 7/1997 | Yorkey | |
| 5,662,106 A | 9/1997 | Swedlow et al. | |
| 5,692,503 A | 12/1997 | Keunstner | |
| 5,758,644 A | 6/1998 | Diab et al. | |
| 5,779,631 A | 7/1998 | Chance | |
| 5,830,139 A | 11/1998 | Abreu | |
| 5,842,981 A | 12/1998 | Larsen et al. | |
| 5,873,821 A | 2/1999 | Chance et al. | |
| 5,995,856 A | 11/1999 | Mannheimer et al. | |
| 6,011,986 A | 1/2000 | Diab et al. | |
| 6,035,223 A | 3/2000 | Baker | |
| 6,064,898 A | 5/2000 | Aldrich | |
| 6,073,101 A | 6/2000 | Maes | |
| 6,120,460 A | 9/2000 | Abreu | |
| 6,134,460 A | 10/2000 | Chance | |
| 6,163,715 A | 12/2000 | Larsen et al. | |
| 6,181,958 B1 | 1/2001 | Steuer et al. | |
| 6,230,035 B1 | 5/2001 | Aoyagi et al. | |
| 6,266,546 B1 | 7/2001 | Steuer et al. | |
| 6,312,393 B1 | 11/2001 | Abreu | |
| 6,359,612 B1 | 3/2002 | Fritz et al. | |
| 6,397,091 B2 | 5/2002 | Diab et al. | |
| 6,415,236 B2 | 7/2002 | Kobayashi et al. | |
| 6,438,399 B1 | 8/2002 | Kurth | |
| 6,445,597 B1 | 9/2002 | Boylan et al. | |
| 6,478,800 B1 | 11/2002 | Fraser et al. | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,615,064 B1 | 9/2003 | Aldrich | |
| 6,622,095 B2 | 9/2003 | Kobayashi et al. | |
| 6,658,277 B2 | 12/2003 | Wasserman | |
| 6,662,030 B2 | 12/2003 | Khalil et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,690,958 B1 | 2/2004 | Walker et al. | |
| 6,693,812 B1 | 2/2004 | Li et al. | |
| 6,708,048 B1 | 3/2004 | Chance | |
| 6,711,424 B1 | 3/2004 | Fine et al. | |
| 6,711,425 B1 | 3/2004 | Reuss | |
| 6,748,254 B2 | 6/2004 | O'Neil et al. | |
| 6,785,568 B2 | 8/2004 | Chance | |
| 6,801,797 B2 | 10/2004 | Mannheimer et al. | |
| 6,801,799 B2 | 10/2004 | Mendelson | |
| 6,842,510 B2 | 1/2005 | Sakamoto | |
| 6,873,865 B2 | 3/2005 | Steuer et al. | |
| 6,934,571 B2 | 8/2005 | Wiesmann et al. | |
| 6,947,780 B2 | 9/2005 | Scharf | |
| 6,949,081 B1 | 9/2005 | Chance | |
| 6,961,448 B2 * | 11/2005 | Nichols et al. | 382/115 |
| 6,961,598 B2 | 11/2005 | Diab | |
| 6,996,427 B2 | 2/2006 | Ali et al. | |
| 7,001,334 B2 | 2/2006 | Reed et al. | |
| 7,024,233 B2 | 4/2006 | Ali et al. | |
| 7,027,849 B2 | 4/2006 | Al-Ali | |
| 7,186,966 B2 | 4/2007 | Al-Ali | |
| 7,209,775 B2 | 4/2007 | Bae et al. | |
| 7,215,991 B2 | 5/2007 | Besson et al. | |
| 7,319,962 B2 | 1/2008 | Goedeke et al. | |
| 7,423,526 B2 | 9/2008 | Despotis | |
| 2001/0005773 A1 | 6/2001 | Larsen et al. | |
| 2001/0020122 A1 | 9/2001 | Steuer et al. | |
| 2001/0032085 A1 * | 10/2001 | Goedeke et al. | 704/275 |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0038081 A1 | 3/2002 | Fein et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0048312 A1 | 3/2003 | Zimmerman et al. | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0140929 A1 * | 7/2003 | Wilkes et al. | 128/898 |
| 2003/0144584 A1 | 7/2003 | Mendelson | |
| 2003/0185358 A1 * | 10/2003 | Sakamoto | 379/102.01 |
| 2003/0195402 A1 | 10/2003 | Fein et al. | |
| 2003/0220548 A1 | 11/2003 | Schmitt | |
| 2003/0220576 A1 | 11/2003 | Diab | |
| 2003/0229499 A1 * | 12/2003 | Von Bosse et al. | 704/275 |
| 2004/0006261 A1 | 1/2004 | Swedlow et al. | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0162472 A1 | 8/2004 | Berson et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0193049 A1 * | 9/2004 | Greenberg | 600/437 |
| 2004/0230106 A1 | 11/2004 | Schmitt et al. | |
| 2005/0010087 A1 | 1/2005 | Banet et al. | |
| 2005/0052275 A1 | 3/2005 | Houle | |
| 2005/0080323 A1 | 4/2005 | Kato | |
| 2005/0101850 A1 | 5/2005 | Parker | |
| 2005/0107676 A1 | 5/2005 | Acosta et al. | |
| 2005/0113656 A1 | 5/2005 | Chance | |
| 2005/0168722 A1 | 8/2005 | Forstner et al. | |
| 2005/0192488 A1 | 9/2005 | Bryenton et al. | |
| 2005/0203357 A1 | 9/2005 | Debreczeny et al. | |
| 2005/0234317 A1 | 10/2005 | Chance et al. | |
| 2005/0234381 A1 | 10/2005 | Guenter et al. | |
| 2005/0242919 A1 | 11/2005 | Wang et al. | |
| 2005/0267346 A1 | 12/2005 | Faber et al. | |
| 2005/0280531 A1 | 12/2005 | Fadem et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0025660 A1 | 2/2006 | Swedlow et al. | |
| 2006/0030762 A1 | 2/2006 | David et al. | |
| 2006/0030763 A1 | 2/2006 | Mannheimer et al. | |
| 2006/0030765 A1 | 2/2006 | Swedlow et al. | |
| 2006/0052680 A1 | 3/2006 | Diab | |
| 2006/0058683 A1 | 3/2006 | Chance | |
| 2006/0058691 A1 | 3/2006 | Kiani | |
| 2006/0069319 A1 | 3/2006 | Elhag et al. | |
| 2006/0074321 A1 | 4/2006 | Kouchi et al. | |
| 2006/0079794 A1 | 4/2006 | Liu et al. | |
| 2006/0132283 A1 | 6/2006 | Eberhart et al. | |
| 2006/0149144 A1 | 7/2006 | Lynn et al. | |
| 2006/0189871 A1 | 8/2006 | Al-Ali et al. | |
| 2006/0195025 A1 | 8/2006 | Ali et al. | |
| 2006/0211932 A1 | 9/2006 | Al-Ali et al. | |
| 2006/0220881 A1 | 10/2006 | Al-Ali et al. | |
| 2006/0226992 A1 | 10/2006 | Al-Ali et al. | |
| 2006/0238358 A1 | 10/2006 | Al-Ali et al. | |
| 2006/0253010 A1 | 11/2006 | Brady et al. | |
| 2006/0276714 A1 | 12/2006 | Holt et al. | |
| 2007/0100633 A1 * | 5/2007 | Ramirez | 704/275 |
| 2007/0106132 A1 | 5/2007 | Elhag et al. | |
| 2007/0106510 A1 * | 5/2007 | Hsing et al. | 704/246 |
| 2007/0106540 A1 | 5/2007 | Kovalcik | |

| | | | |
|---|---|---|---|
| 2007/0203406 A1 | 8/2007 | Anderson et al. | |
| 2007/0270665 A1 | 11/2007 | Yang et al. | |
| 2008/0004513 A1 | 1/2008 | Walker et al. | |
| 2008/0103375 A1 | 5/2008 | Kiani et al. | |
| 2008/0108884 A1 | 5/2008 | Kiani et al. | |
| 2008/0177160 A1 | 7/2008 | Al-Ali et al. | |
| 2008/0194925 A1 | 8/2008 | Alsafadi et al. | |
| 2008/0208009 A1 | 8/2008 | Shklarski | |
| 2008/0298603 A1* | 12/2008 | Smith | 381/67 |

FOREIGN PATENT DOCUMENTS

| | | |
|---|---|---|
| DE | 102 13 692 A1 | 10/2003 |
| EP | 1349146 A | 10/2003 |
| EP | 1643401 | 4/2006 |
| JP | 5-212016 | 8/1993 |
| JP | 2005103316 | 4/2005 |
| WO | WO 92/20273 | 11/1992 |
| WO | WO 94/03102 | 2/1994 |
| WO | WO 97/49330 | 12/1997 |
| WO | WO 01/45553 A1 | 6/2001 |
| WO | WO 0237466 | 5/2002 |
| WO | 2005114524 | 12/2005 |
| WO | 2006006107 | 1/2006 |
| WO | 2006006158 | 1/2006 |
| WO | 2006009830 | 1/2006 |
| WO | WO 06039752 | 4/2006 |
| WO | 2006048840 | 5/2006 |
| WO | 2006051464 | 5/2006 |
| WO | 2006064397 | 6/2006 |
| WO | 2006109072 | 10/2006 |

OTHER PUBLICATIONS

Bongard, Frederic S., et al., "Continuous Dual Oximetry in Surgical critical care—Indications and Limitations," *Annals of Surgery*, vol. 216, No. 1, pp. 60-68 (1992).

Herman, Bruce, MD. et al., "Assessment of Dysphagia with the Use of Pulse Oximetry", Dysphagia 14:152-156; Copyright Springer-Verlag New York Inc. 1999.

Tsien, Christine L., "TrendFinder: Automated Detection of Alarmable Trends", Massachusetts Institute of Technology, Jun. 2000 (241 pages).

Lee, Jason C.S., et al., "Simultaneous Measurement of Percent Carboxyhemoglobin and Functional Oxygen Saturation," IEEE Engineering in Medicine and Biology Society, CH2770-6, vol. 89, pp. 1092-1093, 1989.

ISR, PCT/US2007/020847, 6 pages, mailed Jun. 6, 2008.

* cited by examiner

SYSTEM AND METHOD FOR SECURE VOICE IDENTIFICATION IN A MEDICAL DEVICE

BACKGROUND OF THE INVENTION

1. Field Of The Invention

The present invention relates generally to medical devices and, more particularly, to secure voice identification in the medical devices.

2. Description Of The Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of medical devices have been developed for monitoring physiological characteristics. Such devices provide caregivers, such as doctors, nurses, and/or other healthcare personnel, with the information they need to provide the best possible healthcare for their patients. As a result, such monitoring devices have become an indispensable part of modern medicine.

For example, one technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters and other types of medical devices are typically mounted on stands that are positioned around a patient's bed or around an operating room table. When a caregiver desires to command the medical device (e.g., program, configure, and so-forth) they manipulate controls or push buttons on the medical device itself. The medical device typically provides results or responses to commands on a liquid crystal display ("LCD") screen mounted in an externally visible position within the medical device.

This conventional configuration, however, has several disadvantages. First, as described above, this conventional configuration relies upon physical contact with the medical device to input commands (e.g., pushing a button, turning a knob, and the like). Such physical contact, however, raises several concerns. Among these concerns are that in making contact with the medical device, the caregiver may spread illness or disease from room to room. More specifically, a caregiver may accidentally deposit germs (e.g., bacteria, viruses, and so forth) on the medical device while manipulating the device's controls. These germs may then be spread to the patient when a subsequent caregiver touches the medical device and then touches the patient. Moreover, if medical devices are moved from one patient room to another, germs transferred to the medical device via touch may be carried from one patient room to another. Even in operating rooms where medical devices are typically static, germs may be transferred onto a medical device during one surgery and subsequently transferred off the medical device during a later performed surgery.

Second, beyond contamination, medical devices that rely on physical contact for command input may clutter the caregiver's workspace. For example, because the medical device must be within an arm's length of the caregiver, the medical device may crowd the caregiver—potentially even restricting free movement of the caregiver. In addition, caregivers may have difficulty manipulating controls with gloved hands. For example, it may be difficult to grasp a knob or press a small button due to the added encumbrance of a latex glove.

Third, current trends in general medical device design focus on miniaturizing overall medical device size. However, as controls which rely on physical contact must be large enough for most, if not all, caregivers to manipulate with their hands, medical devices that employ these types of controls are limited in their possible miniaturization. For example, even if it were possible to produce a conventional oximeter that was the size of a postage stamp, it would be impossible to control this theoretical postage stamp-sized pulse oximeter with currently available techniques.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

For at least the reasons set forth above, an improved system or method for interacting with a medical monitoring device would be desirable. A possible solution for resolving one or more of the issues set forth above involves issuing voice commands to the medical device rather than physically manipulating controls. However, this solution raises new concerns.

First, the medical device should not react to simple complaints from patients or visitors. Medical devices often have loud, annoying alarms to alert caregivers that something is wrong. If an alarm sounds, the patient or a visitor typically should not be allowed to tell the medical device to quiet the alarm. In addition, it may be desirable to prevent some medical personnel from performing all of the functions on a given medical device. For example, an orderly typically may not be able to command a medical device to alter a patient's treatment.

Second, in medical devices that store patient information, security measures typically should ensure patient privacy. Some medical devices store historical data on the patient which the caregiver can reference for comparisons. For example, a pulse oximeter may record trends in the patient's blood-oxygen saturation level, so that a caregiver can determine whether treatment is improving the patient's condition. Accordingly, it may be desirable to allow only certain personnel to access the patient's medical history.

One or more of the embodiments set forth below may be directed towards one or more of the issues discussed above.

Figure 1:
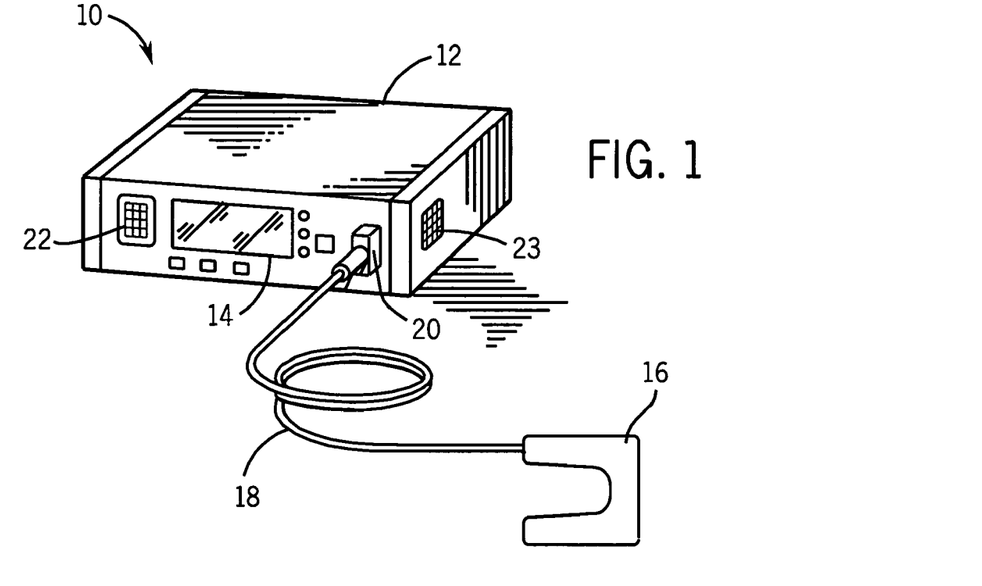
FIG. 1 is a diagrammatical representation of a pulse oximeter featuring an integral microphone in accordance with one embodiment of the present invention.

Turning initially to FIG. 1, an exemplary pulse oximeter featuring an integral microphone in accordance with one embodiment is illustrated and generally designated by the reference numeral 10. The pulse oximeter 10 may include a main unit 12 that houses hardware and/or software configured to calculate various physiological parameters. As illustrated, the main unit 12 may include a display 14 for displaying the calculated physiological parameters, such as oxygen saturation or pulse rate, to a caregiver or patient. In alternate embodiments, as described in further detail below, the display 14 may be omitted from the main unit 12.

The pulse oximeter 10 may also include a sensor 16 that may be connected to a body part (e.g., finger, forehead, toe, or earlobe) of a patient or a user. The sensor 16 may be configured to emit signals or waves into the patient's or user's tissue and detect these signals or waves after dispersion and/or reflection by the tissue. For example, the sensor 16 may be configured to emit light from two or more light emitting diodes ("LEDs") into pulsatile tissue (e.g., finger, forehead, toe, or earlobe) and then detect the transmitted light with a light detector (e.g., a photodiode or photo-detector) after the light has passed through the pulsatile tissue.

As those of ordinary skill in the art will appreciate, the amount of transmitted light that passes through the tissue generally varies in accordance with a changing amount of blood constituent in the tissue and the related light absorption. On a beat-by-beat basis, the heart pumps an incremental amount of arterial blood into the pulsatile tissue, which then drains back through the venous system. The amount of light that passes through the blood-perfused tissue varies with the cardiac-induced cycling arterial blood volume. For example, when the cardiac cycle causes more light-absorbing blood to be present in the tissue, less light travels through the tissue to strike the sensor's photo-detector. These pulsatile signals allow the pulse oximeter 10 to measure signal continuation caused by the tissue's arterial blood, because light absorption from other tissues remains generally unchanged in the relevant time span.

In alternate embodiments, the sensor 16 may take other suitable forms beside the form illustrated in FIG. 1. For example, the sensor 16 may be configured to be clipped onto a finger or earlobe or may be configured to be secured with tape or another static mounting technique. The sensor 16 may be connected to the main unit 12 via a cable 18 and a connector 20.

The pulse oximeter 10 may also include an integral microphone 22. As will be described further below, the integral microphone 22 may be configured to receive voice commands from a caregiver or user that can be processed into commands for the pulse oximeter 10. Although FIG. 1 illustrates the integral microphone 22 as being located on a front facade of the main unit 12, it will be appreciated that in alternate embodiments, the integral microphone 22 may be located at another suitable location on or within the main unit 12.

The pulse oximeter 10 may also include a speaker 23. As will be described further below, the speaker 23 may be configured to broadcast alerts to a caregiver or user. Although FIG. 1 illustrates the speaker 23 as being located on a side facade of the main unit 12, it will be appreciated that in alternate embodiments, the speaker 23 may be located at another suitable location on or within the main unit 12.

Figure 2:
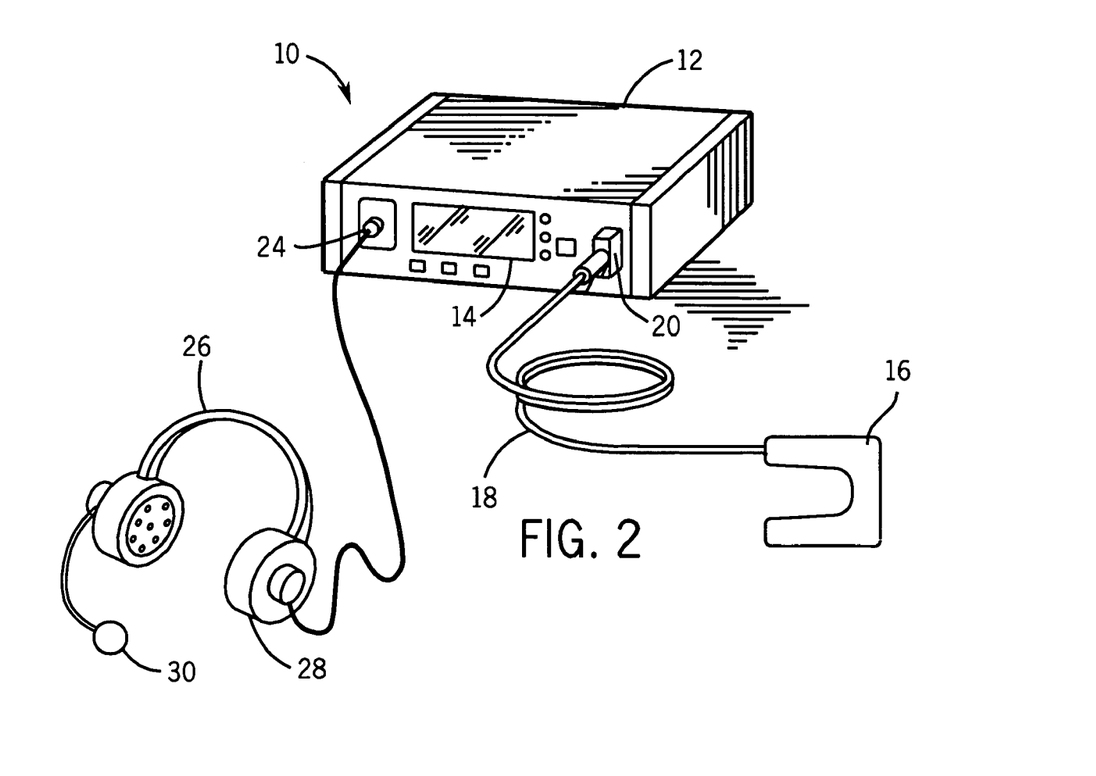
FIG. 2 is a diagrammatical representation of a pulse oximeter featuring an external microphone in accordance with one embodiment of the present invention.

Turning next to FIG. 2, another embodiment of the exemplary pulse oximeter 10 featuring an external microphone and speaker in accordance with one embodiment. For simplicity, like reference numerals have been used to designate those features previously described in regard to FIG. 1. As illustrated in FIG. 2, the pulse oximeter 10 includes the main unit 12, the screen 14, the sensor 16, the cable 18, and the connector 20. However, in place of or in addition to the integral microphone 22, the pulse oximeter 10 illustrated in FIG. 2 includes an audio connector 24 suitable for coupling a headset 26 to the main unit 12.

As illustrated in FIG. 2, the headset 26 may include one or more speakers 28 and an external microphone 30. As will be described further below, the one or more external speakers 28 may be employed by the pulse oximeter 10 to broadcast suitable alerts to a caregiver or user. In addition, the external microphone 30 may be employed to receive voice commands for the pulse oximeter 10.

Figure 3:
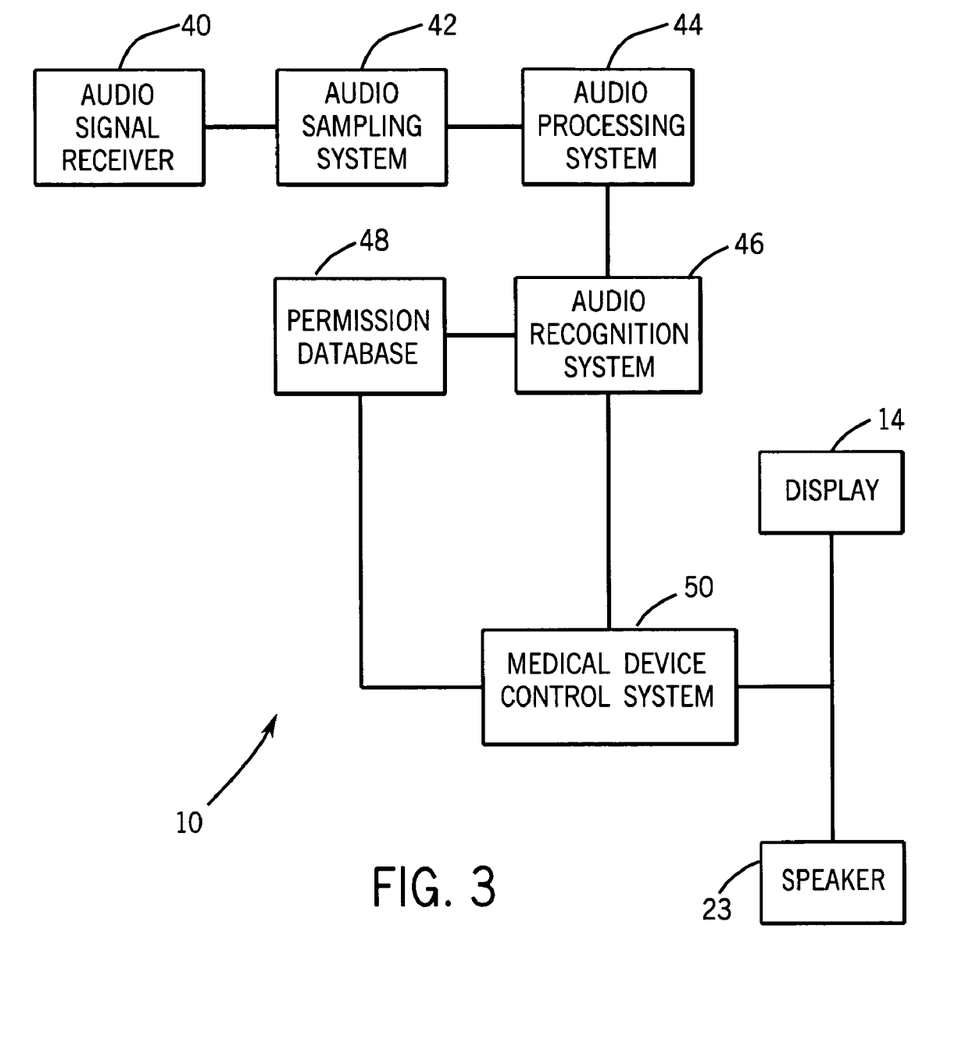
FIG. 3 is a block diagram of a medical device configured for secure user identification in accordance with one embodiment of the present invention.

FIG. 3 is a block diagram of a pulse oximeter 10, configured for secure user identification in accordance with one embodiment. For simplicity, like reference numerals have been used to designate those features previously described with regard to FIGS. 1 and 2. As illustrated in FIG. 3, the pulse oximeter 10 may include a plurality of modules (blocks 40-50). These modules may be hardware, software, or some combination of hardware and software. Additionally, it will be appreciated that the modules shown in FIG. 3 are merely one example and other embodiments can be envisaged wherein the module functions are split up differently or wherein some modules are not included or other modules are included. Moreover, it will be appreciated that the blocks 40-50 may be employed in a plurality of other suitable medical devices in addition to the pulse oximeter 10. For example, the blocks 40-50 may be employed in respirators, ventilators, electroencephalogram ("EEG") devices, medical cutting devices, and so-forth.

As illustrated in FIG. 3, the pulse oximeter 10 may include an audio signal receiver 40. The audio signal receiver 40 may include any suitable form of microphone or voice recording device, such as the integral microphone 22 (illustrated in FIG. 1) or the external microphone 30 (illustrated in FIG. 2). As those of ordinary skill in the art will appreciate, the audio signal receiver 40 may be configured to receive an audio signal (i.e., an acoustic wave) and to convert the audio signal into an electronic analog waveform.

The audio signal receiver 40 may be configured to transmit the analog electrical wave to an audio sampling system 42. The audio sampling system 42 may be configured to sample the electronic analog waveform to create digital voice data. For example, in one embodiment, the audio sampling system 42 may be configured to sample the electronic analog waveform 16,000 times per second to create a digital waveform. In alternate embodiments, other suitable sampling techniques may be employed.

An audio processing system 44 may be configured to receive the digital waveform and to convert the digital waveform into frequencies that can be recognized by an audio recognition system 46. In one embodiment, the audio processing system 44 may be configured to perform a Fast Fourier Transform on the incoming digital waveform to generate a plurality of frequencies. The audio processing system 44 may then transmit the plurality of frequencies to the audio recognition system 46.

The audio recognition system 46 may be pre-populated or programmed with a plurality of frequency combinations that are associated with commands for the pulse oximeter 10. For example, frequency combinations associated with the audio command "turn off alarm" may be associated with a command for the pulse oximeter 10 to silence an alarm. As mentioned above, in one embodiment, the particular frequency combinations may be pre-programmed or pre-configured. However, in alternate embodiments, the frequency combinations may be programmed into the audio recognition system by another suitable system.

In addition, besides recognizing a command for the oximeter 10, the audio recognition system 46 may be configured to identify a particular user based on that user's voice or other distinguishing audio. For example, the audio recognition system 46 might have a stored voiceprint for each authorized user which enables the system 46 to identify the user. In one possible embodiment, this voiceprint might comprise a distinct password or phrase. In another possible embodiment, this voiceprint might comprise a sufficiently extensive sample of the user's speech such that the user may be identified from any word or phrase. These different possible embodiments of the audio recognition system 46 will be discussed further below.

The audio recognition system 46 may also be coupled to a permission database 48. In one possible embodiment, this permission database 48 may assign each user a permission level. The user's permission level would then determine which commands that user can successfully give to the pulse oximeter 10. For example, a user who does not have permission to silence a vital alarm would be unable to do so. The audio recognition system 46 may also be coupled to a medical device control system 50. As will be appreciated by those with ordinary skill in the art, the medical device control system 50 may be configured to control the main unit 12 as well as the sensor 16 to produce physiological monitoring results and/or alarms, which may be transmitted to the display 14 or the speaker 23. Examples of such frequency combinations may include simultaneous combinations of discrete musical pitches or intervals, or sequences of discrete or continuously changing musical pitches or intervals. Sequential frequency combinations may also include corresponding sequences of timing (rhythm), loudness, or other features common to music or speech.

Figure 4:
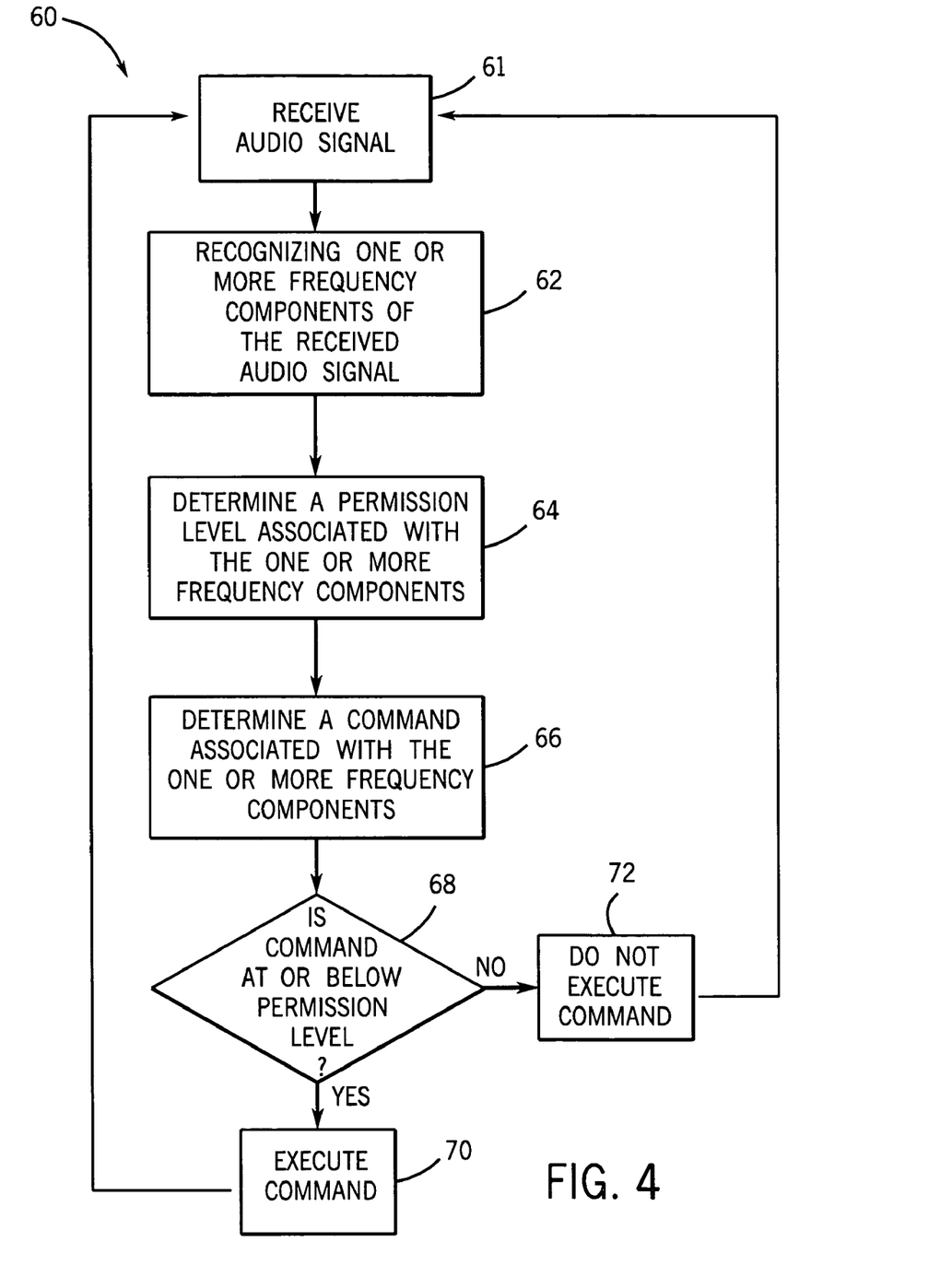
FIG. 4 is a flow chart illustrating an exemplary technique for secure user identification in accordance with one embodiment of the present invention.

FIG. 4 is a flow chart illustrating an exemplary technique 60 for secure user identification in accordance with one embodiment of the present invention. As described further below, the technique 60 may use each command given by the caregiver to both identify the user and control the oximeter 10. In one embodiment, the technique 60 may be executed by the pulse oximeter 10. It will be appreciated, however, that in alternate embodiments, other suitable medical devices may employ the technique 60.

As indicated by block 61, the technique 60 may begin by receiving an audio signal. For example, this audio signal might be a voice command given by a caregiver to silence an alarm emitted by oximeter 10. Next, the audio recognition system 46 may recognize one or more frequency components of the received audio signal and determine the identity of the speaker, as discussed above in regard to FIG. 3 (block 62). The speaker may be then "looked up" in the permission database 48 and assigned a permission level as indicated by block 64. As described above, this permission level may be determined based on the caregiver's role, such as nurse, doctor, or orderly.

Next, the audio recognition system 46 may determine the command associated with the frequency components, as indicated by block 66. For example, the audio recognition system 46 may determine that the one or more frequency components are associated with a command to turn off the pulse oximeter's alarm. Then, as indicated by block 68, the command determined in block 66 may be compared against the permission level (block 64). If the command is at or below the permission level, the command is executed (block 70); whereas if the command is above the permission level, the command is not executed (block 72). Lastly, the technique 70 may cycle back to block 61 to repeat the process for subsequent commands.

Figure 5:
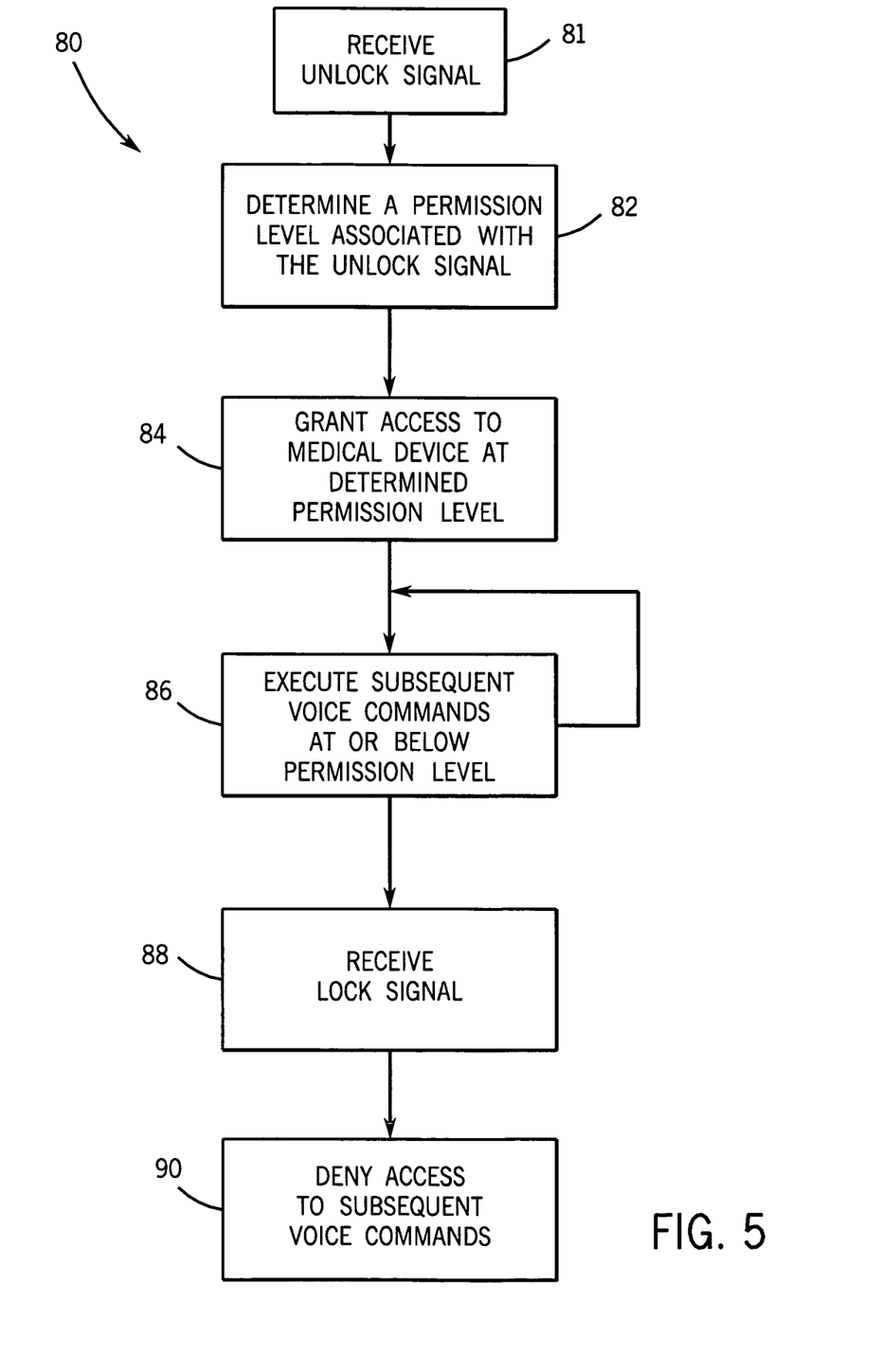
FIG. 5 is a flow chart illustrating another exemplary technique for secure user identification in accordance with one embodiment of the present invention.

FIG. 5 is a flow chart illustrating another exemplary technique 80 for secure user identification in accordance with one embodiment of the present invention. For ease of description, the technique 80 will be described in conjunction with a pulse oximeter 100 illustrated in FIG. 6. It will be appreciated, however, that in alternate embodiments, the technique 80 may be performed by any one of a number of suitable medical devices.

The technique 80 may begin by receiving an unlock signal. For example, in one embodiment, the pulse oximeter 100 may be "unlocked" by an unlock signal provided by the caregiver (block 81). As will be described further below, once unlocked, the pulse oximeter 100 may be configured to accept all voice commands at or below a particular permission level until the pulse oximeter is "locked" again. In one embodiment, the unlock signal may be an audio signal, such as a password, phrase, or any other unique sound. For example, the password may be a foreign or nonsensical word or utterance that is unlikely to be accidentally spoken by a patient, caregiver, or guest. In still another embodiment, this signal may be a magnetic signal from a swipe card. In another embodiment, the unlock signal may be a wireless signal, such as a radio frequency signal, a light signal, or other suitable wireless signal. For example, in one embodiment, the unlock signal may be emitted by an external device 102 (FIG. 6), such as a wireless transmitter, a key fob, a BLUETOOTH device, an access card, and the like.

Next, the technique 80 may include determining a permission level of the unlock signal, as indicated by block 82. This may be accomplished in different ways depending on the form of the unlock signal. For example, in one embodiment using an audio signal, a signal processing system within the pulse oximeter 100 may be configured to determine the permission level based on a permission database, as discussed above in regard to blocks 62 and 64 of FIG. 4. In another embodiment using a radio frequency signal, information on the permission level may be programmed into the signal itself.

Next, the technique 80 may include granting access to the pulse oximeter 100 based on the determined permission level, as indicated by block 84. In other words, the pulse oximeter 100 may be unlocked such that the caregiver is able to control the pulse oximeter 100 (at their permission level) with a voice commands, as indicated by block 86. In one embodiment, voice commands may be employed using one or more of the techniques disclosed in commonly assigned patent application Ser. No. 11/540,457 entitled SYSTEM AND METHOD FOR INTEGRATING VOICE WITH A MEDICAL DEVICE and filed on Sep. 29, 2006, which is hereby incorporated by reference. For example, in one embodiment, once unlocked the audio recognition system 46 may determine the command associated with an audio signal and compare the command against the permission level determined in block 84. If the command is at or below the permission level, the command is executed. This step may be repeated as many times as necessary.

Eventually, when the caregiver is through entering commands, the pulse oximeter 10 may receive a lock signal (block 88). In one embodiment, this lock signal may be the same type of signal as the unlock signal. For example, in one embodiment, reception of the same signal used to unlock the medical device (see block 81 above) may be interpreted as a lock signal. In other words, if the pulse oximeter 100 is locked, the signal is interpreted as an unlock signal and vice-versa. Alternatively, pulse oximeter 100 may be configured to use separate words, commands, and/or signals as the unlock and lock signals. For example, one word may unlock the pulse oximeter 100 and another word may lock it. Further, in one embodiment, the pulse oximeter 100 may also be configured to "relock" itself automatically after a predetermined period of time. For example, the pulse oximeter 100 may be configured to automatically relock if it has not received an unlock command in 10 minutes. As will be appreciated, once locked, the oximeter 10 will not respond to subsequent voice commands (block 90).

Figure 6:
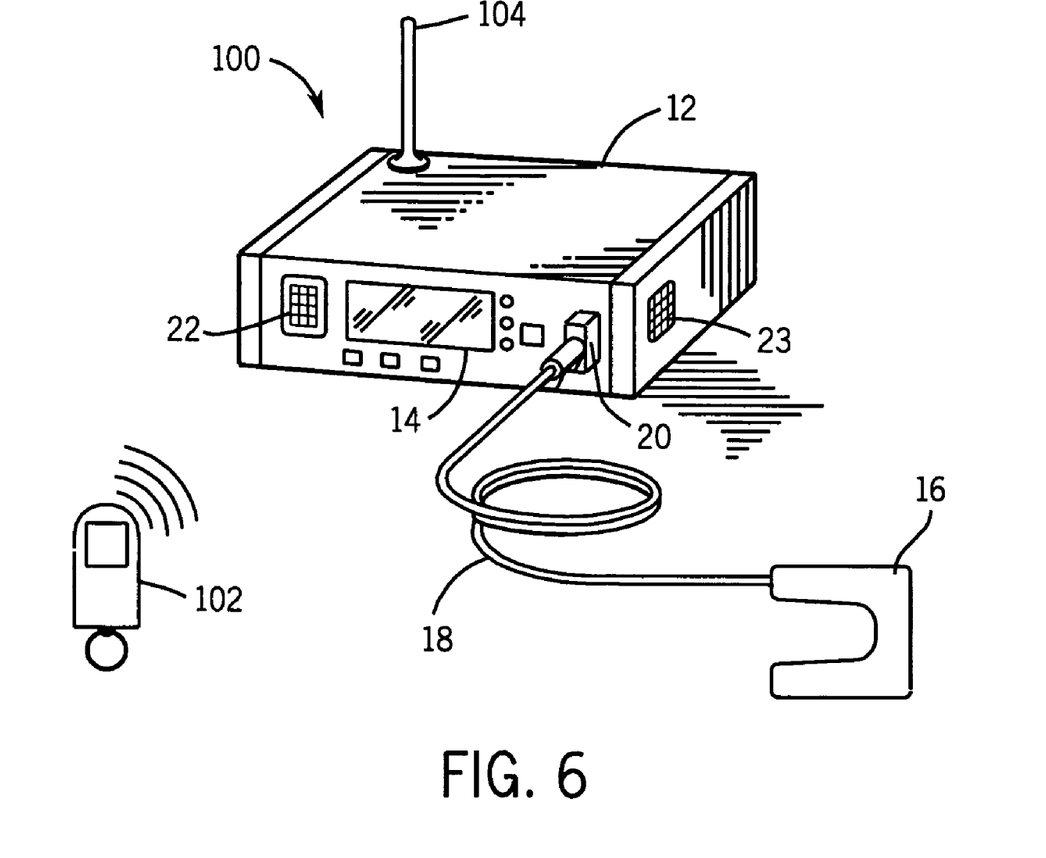
FIG. 6 is a diagrammatical representation of a pulse oximeter and an external device configured to enable commands to the pulse oximeter in accordance with one embodiment of the present invention.

As mentioned above, FIG. 6 is a diagrammatical representation of the pulse oximeter 100 and an external device 102 configured to enable commands to the pulse oximeter 100 in accordance with one embodiment. For simplicity, like reference numerals have been used to designate those features previously described with regard to FIGS. 1 and 2. As illustrated in FIG. 6, the pulse oximeter 100 includes the main unit 12, the screen 14, the sensor 16, the cable 18, and the connector 20. However, as discussed above in regard to FIG. 5, the pulse oximeter 100 may be unlocked or locked by a wireless signal. For this reason, in one embodiment, the external device 102 may be configured to emit an unlock and/or lock signal. For example, the external device 102 may be configured to emit a single signal, which may be interpreted as either an unlock signal or a lock signal depending on when it is received. For example, if the pulse oximeter 100 is locked, the signal is interpreted as an unlock signal and vice-versa. Alternatively, the external device 102 may have separate lock and unlock buttons and may be configured to zemit either a lock signal or an unlock signal depending on which button is depressed.

As the pulse oximeter 100 is configured to receive one or more wireless signals, it may also include an antenna 104 to enable reception of the unlock/lock signal(s) generated by the external device 102. As those of ordinary skill in the art will appreciate, this antenna 104 may be either external or internal in various embodiments.

Figure 7:
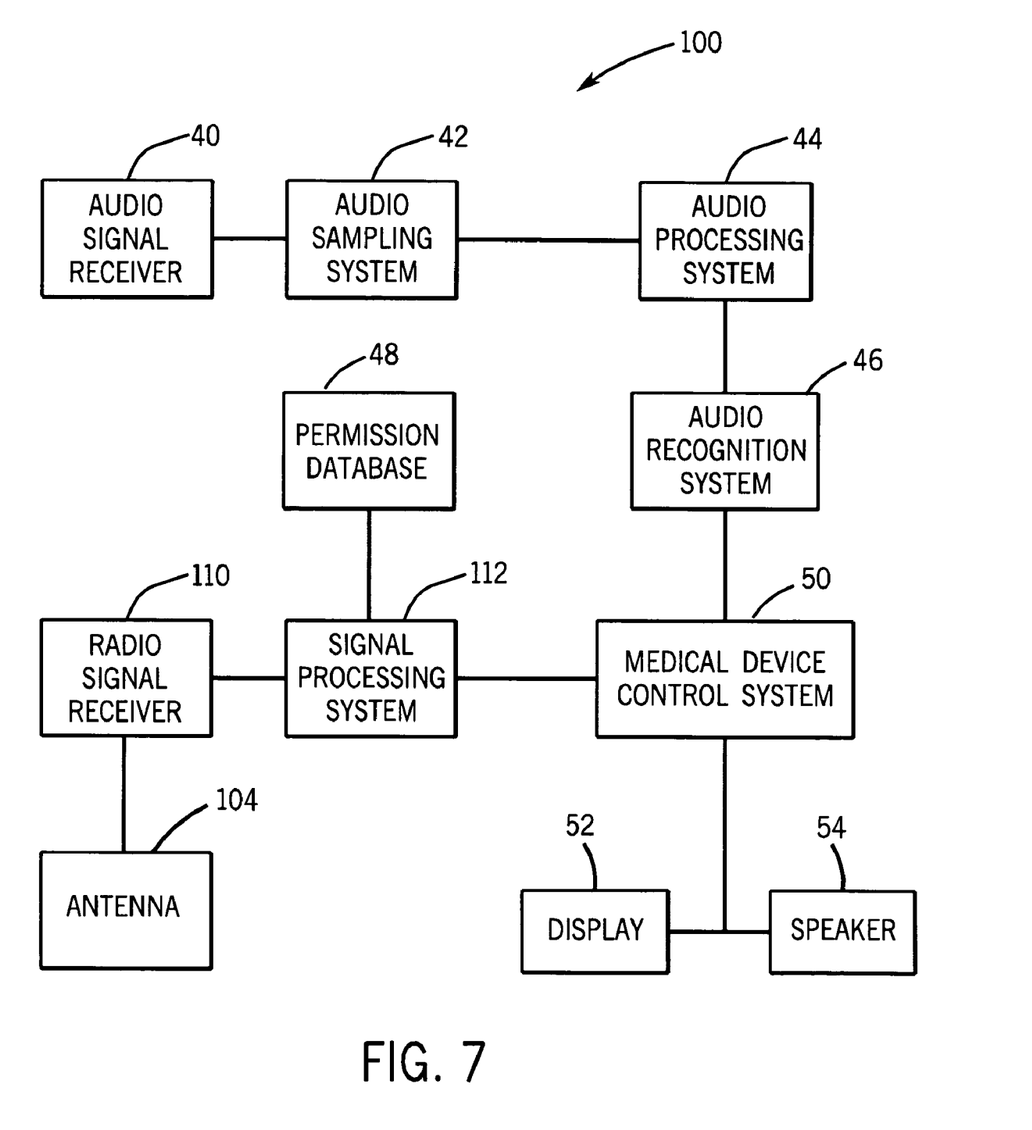
FIG. 7 is a block diagram of a medical device configured for secure user identification in accordance with one embodiment of the present invention.

Turning next to FIG. 7, a block diagram of the pulse oximeter 100 configured for secure user identification in accordance with one embodiment is illustrated. For simplicity, like reference numerals have been used to designate those features previously described in regard to FIG. 3. As illustrated in FIG. 7, the pulse oximeter 100 may include a plurality of modules (blocks 40-54, 104, and 110-112). These modules may be hardware, software, or some combination of hardware and software. Additionally, it will be appreciated that the modules shown in FIG. 7 are merely one example and other embodiments can be envisaged wherein the module functions are split up differently or wherein some modules are not included or other modules are included. Moreover, it will be appreciated that the blocks 40-54, 104, and 110-112 may be employed in a plurality of other suitable medical devices in addition to the pulse oximeter 100. For example, the blocks 40-54 and 110-112 may be employed in respirators, ventilators, electroencephalogram ("EEG") devices, medical cutting devices, and so-forth.

As illustrated in FIG. 7, in addition to the modules 40-54, which were described in detail above, the pulse oximeter 100 may also include a radio signal receiver 110, which may be coupled to the antenna 104. As those of ordinary skill in the art will appreciate, the radio signal receiver 110 may be configured to receive the radio signal generated by the external device 102 and to convert the radio signal into an electronic pulse. This electronic pulse may then be transmitted to a signal processing system 112, which may be configured to decode the electronic pulse and determine a permission level associated with the electronic pulse based on the permission database 48. Once a permission level has been determined, this permission level may be transmitted to the medical device control system 50, which may be configured to execute those voice commands at or below the determined permission level until a "lock" command is received, as described above in regard to FIGS. 5 and 6. In this way, the caregiver may unlock the pulse oximeter 100 when he or she wished to issue voice commands to the pulse oximeter 100, and relock the pulse oximeter 100 to prevent authorized persons (e.g., patients) from giving the pulse oximeter 100 commands, when he or she is done.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, as described above the present techniques may not only be applied to pulse oximeters, but also to a number of other suitable medical devices

What is claimed is:

1. A method comprising:
receiving an audio signal in a medical device;
identifying a voice of a user from the received audio signal;
determining a first permission level based at least in part on a role associated with the user;
determining a medical device command associated with the audio signal, wherein the medical device command has a second permission level; and
executing the medical device command if the second permission level is at or below the first permission level.

2. The method, as set forth in claim 1, wherein determining the first permission level comprises determining a permission level associated with a doctor, nurse, orderly, or patient.

3. The method, as set forth in claim 1, comprising rejecting the medical device command if the second permission level is above the first permission level.

4. The method, as set forth in claim 1, wherein determining the first permission level comprises determining if the user is a caregiver.

5. The method, as set forth in claim 1, wherein executing the medical device command comprises executing a pulse oximeter command.

6. A medical device comprising:
an audio processing system configured to process a voice command into voice command data;
an audio recognition system configured to identify the voice command as spoken by one of a plurality of voices based at least in part on the voice command data, wherein the audio recognition system is configured to determine a command for the medical device from the voice command data, wherein the command has an associated permission level;
a permission database configured to store a permission level associated with one or more of the plurality of voices, wherein the permission level is based at least in part on a medical role associated with the one or more of the plurality of voices; and
a control system configured to determine the permission level associated with the medical role based on the permission database, wherein the control system is configured to execute the determined command if the permission level of the determined command is at or below the permission level associated with the medical role.

7. The medical device, as set forth in claim 6, wherein the medical device comprises a pulse oximeter.

8. The medical device, as set forth in claim 6, comprising an audio receiver configured to receive the voice command, wherein the audio receiver is coupled to the audio processing system.

9. A method of operating a medical device comprising:
receiving an unlock signal in the medical device, wherein the unlock signal is configured to allow operational parameters of the medical device to be altered;
determining a permission level associated with the unlock signal;
receiving a voice command in the medical device;
determining permission level associated with the received voice command; and
executing the received voice command in the medical device if its permission level is at or below the permission level associated with the unlock signal.

10. The method, as set forth in claim 9, comprising:
receiving a lock signal in the medical device, wherein the lock signal is configured to disallow operational parameters of the medical device to be altered; and
rejecting a voice command in the medical device after receiving the lock signal.

11. The method, as set forth in claim 9, wherein receiving the unlock signal comprises receiving a wireless signal.

12. The method, as set forth in claim 11, wherein receiving the wireless signal comprises receiving a radio frequency signal.

13. The method, as set forth in claim 9, wherein receiving the unlock signal comprises receiving an audio password.

14. The method, as set forth in claim 13, wherein receiving the audio password comprises receiving a non-English utterance.

15. The method, as set forth in claim 9, wherein receiving the unlock signal comprises receiving a BLUETOOTH signal.

16. A medical device configured to:
receive an unlock signal configured to allow operational parameters of the medical device to be altered;
determine a permission level associated with the unlock signal;
receive a voice command;
determine permission level associated with the received voice command; and
execute the received voice command if its permission level is at or below the permission level associated with the unlock signal.

17. The medical device, as set forth in claim 16, comprising a signal processing system, wherein the signal processing system is configured to determine the permission level associated with the unlock signal.

18. The medical device, as set forth in claim 16, comprising an antenna coupled to the signal processing system.

19. The medical device, as set forth in claim 16, comprising an external device, wherein the external device is configured to generate the unlock signal.

20. The medical device, as set forth in claim 19, wherein the external device comprises a keyfob.

21. The medical device, as set forth in claim 19, wherein the external device comprises a BLUETOOTH device.

22. The medical device, as set forth in claim 16, wherein the medical device is configured to receive an audio unlock signal.

23. The medical device, as set forth in claim 22, wherein the audio unlock signal comprises non-English utterance.

24. The medical device, as set forth in claim 16, wherein the medical device comprises a pulse oximeter.

* * * * *